United States Patent [19]

Wehrenberg

[11] Patent Number: 5,081,272

[45] Date of Patent: Jan. 14, 1992

[54] PROCESS FOR PREPARATION OF PHOSPHORODICHLOROTHIOATES

[75] Inventor: Peter K. Wehrenberg, Oakland, Calif.

[73] Assignee: Imperial Chemical Industries PLC, Millbank, England

[21] Appl. No.: 569,884

[22] Filed: Aug. 20, 1990

[51] Int. Cl.$^5$ ............................................... C07F 9/20
[52] U.S. Cl. ..................................... 558/90; 558/144
[58] Field of Search ................................. 558/90, 144

[56] References Cited

U.S. PATENT DOCUMENTS 4,056,581 11/1977 Bayer et al. ............................ 558/90

Primary Examiner—Mukund J. Shah
Assistant Examiner—Yogendra Gupta
Attorney, Agent, or Firm—Denis A. Polyn; Lynn Marcus-Wyner

[57] ABSTRACT

An improved process for preparing a phosphorodichlorothioate of the formula

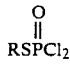

$$\underset{\text{RSPCl}_2}{\overset{\text{O}}{\|}}$$

wherein R is: a $C_1$–$C_{10}$ alkyl group, optionally substituted with a $C_1$–$C_4$ alkoxy group, a $C_1$–$C_4$ Alkylthio group, or a halogen group; a $C_3$–$C_6$ cycoalkyl group; a $C_7$–$C_{10}$ araklyl group, optionally substituted with up to three $C_1$–$C_5$ alkyl groups, $C_1$–$C_4$ alkoxy groups, halogen groups or nitro groups, $C_6$–$C_{10}$ aryl group, optionally substituted with up to three $C_3$–$C_5$ alkyl groups, $C_1$–$C_4$ alkoxy groups, halogen groups or nitro groups; which comprises reacting, at a temperature of from about $-20°$ C. to about 20° C., a mercaptan of the formula R—SH, wherein R is as previously defined, with at least one chlorinating agent, sulfur based acid and phosphorus trichloride. The compounds produced by this process are useful as intermediates in the preparation of O,S-disubstituted phosphorodichloridothiolates, which are, in turn, useful in the preparation of organophosphorus pesticides.

15 Claims, No Drawings

PROCESS FOR PREPARATION OF PHOSPHORODICHLOROTHIOATES

BACKGROUND OF THE INVENTION

1. Field of the Invention

This invention relates to an improved process for the preparation of S-substituted phosphorodichlorothioates, which are useful as intermediates for the manufacture of insecticides.

2. Description of the Related Art

The compounds produced by this process are useful as intermediates in the preparation of O,S-disubstituted phosphorochloridothioates, which are, in turn, useful in the preparation of organophosphorus pesticides described in, for example, U.S. Pat. Nos. 3,374,293, 3,784,654 and 3,839,509. The phosphorodichlorothioates of the present invention can be converted to O,S-disubstituted phosphorochlorothioates by reacting them with an alcohol in the presence of an acid scavenger (i.e., a tertiary amine).

There are many known processes for preparing phosphorodichlorothioates, and the following references are illustrative of these processes: Synthesis of alkyl dichlorodithiophosphates, Izv. Akad. Nauk SSSR, Ser. Khim., (11), 2620-22; Synthesis and fungicidal activity of O,O-diaryl S-isopropyl phosphorothioates, Proc. Indian Natl. Sci. Acad., Part B, 54(4), 287-90; Process for preparing dichlorophosphorothioate esters, German Offen. 3716993; Preparation of alkyl phosphorodithioates, RO 91261; Process for preparing a S-substituted phosphorochloridothiolate, Eur. Pat. Appl. 219770; Efficacy of diaryl S-ethyl phosphorothiolates against root-knot nematode, Indian J. Agric. Sci., 56(8), 5976 05; O-Trihaloethyl phosphorodithioate pesticides, U.S. Pat. No. 4,457,923; S-tert-Alkyl phosphoroamidodithioate pesticides, U.S. Pat. No. 4,450,158; Oxidation of organophosphorus compounds, Ger. Offen. 3,033,957; Sulfuric acid derivatives as attractive oxidation agents for phosphorus (III) Compounds, Angew. Chem., 94(7), 560; Lower S-alkyldichlorothiophosphates, Czech Patent 189,342; Alkyl and aryl phosphorochloridothioates, Japanese Patent 55139394; Organophosphorus compounds, Ger. Offen. 2,635,931; Sulfenyl- and sulfinylphosphonic dichloride insecticides, U.S. Pat. No. 3,454,679; S-Substituted phosphorodichloridothioates, U.S. Pat. No. 3,337,658.

U.S. Pat. No. 4,056,581 describes the preparation of certain S-alkyl, -cycloalkyl, -aralkyl, and -aryl phosphorodichloridothiolates by reacting a sulfenyl chloride, which can be prepared in situ, with phosphorus trichloride and a carboxylic acid or water. This reference utilizes either water or a carboxylic acid as an oxygen donor. In the referenced process, one equivalent of sulfuryl chloride is consumed and one equivalent of carboxylic acid chloride or hydrogen chloride is generated as a byproduct (which must be removed, neutralized and disposed of). The present invention, unlike the process disclosed in U.S. Pat. No. 4,056,581, replaces half of the sulfuryl chloride with an inexpensive sulfur based acid which also serves as the full equivalent of the oxygen donor; therefore, no carboxylic acid chloride is generated, thereby obviating problems of its removal, neutralization and disposal.

BRIEF SUMMARY OF THE INVENTION

Applicant's invention relates to a process for preparing a phosphorodichlorothioate of the formula

wherein R is a $C_1-C_{10}$ alkyl group, optionally substituted with a $C_1-C_4$ alkoxy group, a $C_1-C_4$ alkylthio group or a halogen group; a $C_3-C_6$ cycloalkyl group; a $C_7-C_{10}$ aralkyl group, optionally substituted with up three $C_1-C_5$ alkyl groups, $C_1-C_4$ alkoxy groups, halogen groups or nitro groups; a $C_6-C_{10}$ aryl group, optionally substituted with up to three $C_1-C_5$ alkyl groups, $C_1-C_4$ alkoxy groups, halogen groups or nitro groups; which comprises reacting, at a temperature of from about $-20°$ C. to about $20°$ C., a mercaptan of the formula R—SH, wherein R is as previously defined, with at least one chlorinating agent, a sulfur based acid and phosphorus trichloride.

DESCRIPTION OF INVENTION

The present invention relates to an improved process for preparing a phosphorodichlorothioate of the formula

wherein R is a $C_1-C_{10}$ alkyl group, optionally substituted with a $C_1-C_4$ alkoxy group, a $C_1-C_4$ alkythio group, or a halogen group; a $C_3-C_6$ cycloalkyl group; a $C_7-C_{10}$ aralky group, optionally substituted with up to three $C_1-C_5$ alkyl groups, $C_1-C_4$ alkoxy groups, halogen groups or nitro groups; a $C_6-C_{10}$ aryl group, optionally substituted wi three $C_1-C_5$ alkyl groups, $C_1-C_4$ alkoxy groups, halogen groups or nitro groups; which comprises reacting, at a temperature of from about $-20°$ C. to about $20°$ C., a mercaptan of the formula R—SH, wherein R is as previously defined, with at least one chlorinating agent, a sulfur based acid and phosphorus trichloride.

In a preferred embodiment of this invention, R is a $(C_1-C_7)$ alkyl group, especially a $(C_2-C_4)$ alkyl group. As used in the specification and claims, the terms alkyl, alkoxy, alkylthio, and aralkyl refer to groups having straight or branched chain spatial configuration.

The process of the present invention involves reacting a mercaptan of the formula:

wherein R is as defined for Formula I, with phosphorus trichloride, a chlorinating agent and sulfur based acid to give a compound of Formula I.

The present process can be represented by the following reaction Scheme (A), which is presented for illustrative purposes only:

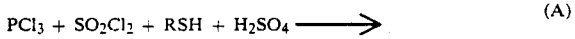

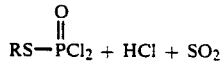

The process can be carried out neat or with a solvent. Suitable solvents include aromatic hydrocarbons such as benzene, toluene, and xylene; aromatic and aliphatic halogenated hydrocarbons such as chlorobenzene, chloroform, carbon tetrachloride, and perchloroethylene; carboxylic acid esters such as ethyl acetate and butyl acetate; and the like.

The reaction is normally conducted at a temperature range of about $-20°$ C. to about 20° C. and preferably at about $-10°$ C. to about 0° C. Generally, a substantially equimolar ratio of reactants is preferred (except for the chlorinating agent and $H_2SO_4$, for which half molar quantities are preferred), though up to 100% molar excesses of any of the reactants can be employed.

The reaction products are obtained by fractional distillation at reduced pressures or by other conventional techniques. The products thus obtained can be used in additional syntheses without further purification.

The reactants can be combined in any order, provided that the chlorinating agent is added to the mercaptan before the phosphorus trichloride. A preferred sequence involves (a) combining the mercaptan and the chlorinating agent (b) adding the phosphorus trichloride and then (c) adding the sulfur based acid.

Reaction conditions such as choice of solvents and temperature correspond to the conditions described above for Scheme (A). Up to 100% molar excesses of any of the reagents can be employed, but the preferred molar ratios are as follows: about 1.0 $PCl_3$; about 0.5 $SO_2Cl_2$; about 1.0 propyl mercaptan; and about 0.5 $H_2SO_4$.

Representative chlorinating agents include chlorine, sulfuryl chloride, N-chlorosuccinimide and the like. Sulfuryl chloride is the most preferred.

Sulfur based acids are sulfur-containing organic and inorganic acids. Representative sulfur based acids include sulfuric acid, chlorosulfonic acid, methylsulfonic acid and the like. Sulfuric acid is the most preferred.

The reaction products can be obtained by fractional distillation at reduced pressures or by other conventional techniques. The products obtained can be used in additional syntheses without further purification.

When the starting materials shown below in Column I are utilized in the preferred process of this invention, the corresponding products shown in Column II are obtained.

I methyl mercaptan
ethyl mercaptan
n-propyl mercaptan
isopropyl mercaptan
n-butyl mercaptan
isobutyl mercaptan
sec-butyl mercaptan
n-amyl mercaptan
n-hexyl mercaptan
n-decyl mercaptan
2-(n-propoxyethyl) mercaptan
2-methylthio-n-propyl mercaptan
2-chloroethyl mercaptan
cyclohexyl mercaptan
benzyl mercaptan
2-chlorophenethyl mercaptan
thiophenol
2-methyl thiophenol
4-ethyl thiophenol
3,5-dimethyl-4-methoxy thiophenol
4-ethoxy thiophenol
3-bromo thiophenol
4-chloro thiophenol
2,5-dichloro thiophenol
2,4,6-thrichloro thiophenol
2,4-dichloro-6-methyl thiophenol
2-chloro-4-propoxy thiophenol
2-chloro-4-bromo thiophenol
4-fluoro thiophenol
4-nitro thiophenol
2-nitro-4-chloro thiophenol
2-nitro-4-methyl thiophenol
naphthyl mercaptan
3,5-dimethylnaphthyl mercaptan
3-chloronapthyl mercaptan

II

S-methyl phosphorodichloridothiolate
S-ethyl phosphorodichloridothiolate
S-n-propyl phosphorodichloridothiolate
S-isopropyl phosphorodichloridothiolate
S-n-butyl phosphorodichloridothiolate
S-isobutyl phosphorodichloridothiolate
S-sec-butyl phosphorodichloridothiolate
S-n-decyl phosphorodichloridothiolate
S-n-amyl phosphorodichloridothiolate
S-n-hexyl phosphorodichloridothiolate
S-2-(n-propoxyethyl)phosphorodichloridothiolate
S-2-methylthio-n-propyl phosphorodichloridothiolate
S-2-chloroethyl phosphorodichloridothiolate
S-cyclohexyl phosphorodichloridothiolate
S-benzyl phosphorodichloridothiolate
S-2-chloro-phenethyl phosphorodichloridothiolate
S-phenyl phosphorodichloridothiolate
S-(2-methylphenyl) -phosphorodichloridothiolate
S-(4-ethylphenyl) phosphorodichloridothiolate
S-(3,5-dimethyl-4-methoxyphenyl) phosphorodichloridothiolate
S-(4-ethoxyphenyl) phosphorodichloridothiolate
S-(3-bromophenyl) phosphorodichloridothiolate
S-(4-chlorophenyl) phosphorodichloridothiolate
S-(2,5-dichlorophenyl) phosphorodichloridothiolate
S-(2,4,6-trichlorophenyl) phosphorodichloridothiolate
S-(2,4-dichloro-6-methylphenyl) phosphorodichloridothiolate
S-(2-chloro-4-propoxyphenyl) phosphorodichloridothiolate
S-(2-chloro-4-bromophenyl)phosphorodichloridothiolate
S-(4-fluorophenyl) phosphorodichloridothiolate
S-(4-nitrophenyl) phosphorodichloridothiolate
S-(2-nitro-4-chlorophenyl) phosphorodichloridothiolate
S-(2-nitro-4-methylphenyl) phosphorodichloridothiolate
S-naphthyl phosphorodichloridothiolate
S-(3,5-dimethylnaphthyl) phosphorodichloridothiolate
S-(3-chloronaphthyl) phosphorodichloridothiolate and the like.

All of the starting materials used in the preparation of the compounds of this invention are known compounds or are readily prepared by methods available to those skilled in the art.

The following example illustrates, without limitation of the scope of the present invention, a preferred process of this invention.

EXAMPLE I

A 3 L four-necked round-bottomed flask was equipped with a mechanical stirrer, an addition funnel topped by a nitrogen bubbler, a thermometer, and a cooling bath. The flask was charged with propanethiol (543 mL, 6.0 moles) and cooled to $-10°$ C. Sulfuryl chloride (241 mL, 3.0 moles) was added over 60 min. while maintaining the temperature at $-5°$ to $-10°$ C. (Caution: rapid evolution of HCl gas!). Phosphorous trichloride (524 mL, 6.0 moles) was added over 30 min. while maintaining the temperature at $-13°$ C. to $-10°$ C. (Caution: evolution of HCl gas!). Sulfuric acid (160 mL, 3.0 moles) was added over 25 min. while maintaining the temperature at $-11°$ C. (Caution: evolution of HCl gas!). The solution was allowed to warm to room temperature overnight (Caution: rapid evolution of HCl gas as the solution warms!). The solution was stripped to remove volatiles and obtain 1061 g of orange oil. A portion of this material (101.3 g) was distilled collecting 83.9 g of colorless oil bp $113°-114°$ C. at 26 mmHg pressure. The product was identified as S-propyl phosphorodichloridothioate contaminated with dipropyl disulfide by GC/MS.

What is claimed is:

1. A process for preparing a phosphorodichlorothioate of the formula

$$RSPCl_2$$

wherein R is a $C_1-C_{10}$ alkyl group, optionally substituted with a $C_1-C_4$ alkoxy group, a $C_1-C_4$ alkylthio group, or a halogen group; a $C_3-C_6$ cycloalkyl group; a $C_7-C_{10}$ aralkyl group, optionally substituted with up to three $C_1-C_5$ alkyl groups, $C_1-C_4$ alkoxy groups, halogen groups or nitro groups; a $C_6-C_{10}$ aryl group, optionally substituted with up to three $C_1-C_5$ alkyl groups, $C_1-C_4$ alkoxy groups, halogen groups or nitro groups; which comprises reacting, at a temperature of from about $-20°$ C. to about $20°$ C., a mercaptan of the formula R—SH, wherein R is as previously defined, with at least one chlorinating agent, sulfuric acid and phosphorus trichloride.

2. A process according to claim 1, wherein R is a $C_1-C_{10}$ alkyl group optionally substituted with a $C_1-C_4$ alkoxy group, a $C_1-C_4$ alkylthio group, or a halogen group.

3. A process according to claim 1, wherein R is a $C_3-C_6$ cycloalkyl group.

4. A process according to claim 1, wherein R is a $C_7-C_{10}$ aralkyl group optionally substituted with up to three $C_1-C_5$ alkyl groups, $C_1-C_4$ alkoxy groups, halogen groups or nitro groups.

5. A process according to claim 1, wherein R is a $C_6-C_{10}$ aryl group, optionally substituted with up to three $C_1-C_5$ alkyl groups, $C_1-C_4$ alkoxy groups, halogen groups or nitro groups.

6. A process according to claim 1, wherein R is a $C_1-C_6$ alkyl group.

7. A process according to claim 1, wherein R is an n-propyl group.

8. A process according to claim 1, wherein said chlorinating agent is chlorine, sulfuryl chloride, or N-chlorosuccinimide.

9. A process according to claim 1, wherein said chlorinating agent is sulfuryl chloride.

10. A process according to claim 1, wherein R is a $C_1-C_5$ alkyl group, and said chlorinating agent is sulfuryl chloride.

11. A process according to claim 1, wherein R is an n-propyl group, and said chlorinating agent is sulfuryl chloride.

12. A process according to claim 1, wherein said temperature is from about $-20°$ C. to about $20°$ C.

13. A process according to claim 1, wherein said temperature is from about $-10°$ to about $0°$ C.

14. A process according to claim 1, wherein 1.0 equivalent of mercaptan is reacted with 0.5 to 1.0 equivalents of chlorinating agent, 0.5 to 1.0 equivalents of sulfuric acid and 1.0 equivalent of phosphorus trichloride.

15. A process according to claim 1, wherein one equivalent of propyl mercaptan is reacted with one-half equivalent of sulfuryl chloride, one-half equivalent of sulfuric acid and one equivalent of phosphorus trichloride at a temperature from about $-10°$ C. to about $0°$ C.

* * * * *